US012630580B2

(12) United States Patent
Garcia Garcia et al.

(10) Patent No.: US 12,630,580 B2
(45) Date of Patent: May 19, 2026

(54) 5'-O-PHENYLACETYLURIDINE AND THERAPEUTIC USE

(71) Applicant: PHARMA CINQ, LLC, Rockville, MD (US)

(72) Inventors: Rolando Alejandro Garcia Garcia, Germantown, MD (US); Joel A. Saydoff, Vista, CA (US); David Michael Simpson, North Bethesda, MD (US); Reid Warren von Borstel, Potomac, MD (US)

(73) Assignee: PHARMA CINQ, LLC, Rockville, MD (US)

( * ) Notice: Subject to any disclaimer, the term of this patent is extended or adjusted under 35 U.S.C. 154(b) by 327 days.

(21) Appl. No.: 18/036,744

(22) PCT Filed: Nov. 30, 2021

(86) PCT No.: PCT/US2021/061053

§ 371 (c)(1),
(2) Date: May 12, 2023

(87) PCT Pub. No.: WO2022/119784

PCT Pub. Date: Jun. 9, 2022

(65) Prior Publication Data

US 2023/0416292 A1 Dec. 28, 2023

Related U.S. Application Data

(60) Provisional application No. 63/119,764, filed on Dec. 1, 2020.

(51) Int. Cl.
*C07H 19/067* (2006.01)
*A61K 9/00* (2006.01)

(52) U.S. Cl.
CPC ......... *C07H 19/067* (2013.01); *A61K 9/0053* (2013.01)

(58) Field of Classification Search
CPC .............. C07H 19/067; A61K 31/7072; A61K 9/0053; A61P 1/16
See application file for complete search history.

(56) References Cited

U.S. PATENT DOCUMENTS

| | | | | |
|---|---|---|---|---|
| 5,585,512 | A | 12/1996 | Yamazaki et al. | |
| 7,709,459 | B2 * | 5/2010 | von Borstel | A61P 3/00 514/49 |
| 7,915,233 | B1 | 3/2011 | von Borstel | |
| 9,566,257 | B2 | 2/2017 | Jalan et al. | |
| 2001/0025032 | A1 | 9/2001 | von Borstel et al. | |
| 2004/0102523 | A1 | 5/2004 | Broquaire et al. | |
| 2012/0259016 | A1 * | 10/2012 | Jalan | A61P 7/04 514/564 |
| 2014/0142186 | A1 * | 5/2014 | Scharschmidt | A61P 25/00 514/568 |
| 2018/0318381 | A1 | 11/2018 | Vockley et al. | |
| 2023/0357304 | A1 | 11/2023 | Borstel et al. | |
| 2024/0158431 | A1 | 5/2024 | Von Borstel et al. | |

FOREIGN PATENT DOCUMENTS

| | | | | |
|---|---|---|---|---|
| CN | 1031536 | A | 3/1989 | |
| EA | 018007 | B1 | 4/2013 | |
| EP | 3335735 | A1 | 6/2018 | |
| JP | H0232094 | A | 2/1990 | |
| JP | 2002-523434 | A | 7/2002 | |
| JP | 2007-510734 | A | 4/2007 | |
| KR | 10-0818202 | B1 | 3/2008 | |
| RU | 2659388 | C1 | 7/2018 | |
| WO | 2000/050043 | A1 | 8/2000 | |
| WO | 2013/012760 | A1 | 1/2013 | |
| WO | 2014/160502 | A1 | 10/2014 | |
| WO | 2016/028894 | A1 | 2/2016 | |
| WO | 2019/152776 | A1 | 8/2019 | |
| WO | 2022/056428 | A1 | 3/2022 | |
| WO | WO-2022089612 | A1 * | 5/2022 | A61K 31/7064 |
| WO | 2022/119784 | A1 | 6/2022 | |
| WO | 2022/177740 | A1 | 8/2022 | |

OTHER PUBLICATIONS

Oxford English Dictionary, definition of "prevent"; accessed Sep. 9, 2025. (Year: 2025).*
Caldovic, L.; et al. "Genotype-Phenotype Correlations in Ornithine Transcarbamylase Deficiency: A Mutation Update" Journal of Genetics and Genomics 2015, vol. 42, pp. 181-194. (Year: 2015).*
English language machine translation of WO 2022089612 A1; translated Sep. 11, 2025. (Year: 2025).*
Foreign priority application of WO 2022089612 A1 (CN 202011196732.4; filing date of Oct. 30, 2020). (Year: 2020).*
English language machine translation of foreign priority application of WO 2022089612 A1 (CN 202011196732.4; filing date of Oct. 30, 2020). (Year: 2020).*
Livingston, E. H.; et al. "Body surface area prediction in normal-weight and obese patients", American Journal of Physiology—Endocrinology and Metabolism 2001, vol. 281, E586-E591. (Year: 2001).*
Database Pubchem, PubChem CID: 9913736, Available Date: Oct. 25, 2006. <https://pubchem.ncbi.nlm.nih.gov/compound/9913736>.
Mcgregor et al., "Alkaline Bromine Oxidation of Amino Acids and Peptides: Formation of a-Ketoacyl Peptides and Their Cleavage by Hydrogen Peroxide," Biochemistry 1(1):53-60 (1962).
Kubasov et al., "Chemical kinetics and catalysis. Part 1," Moscow University Publishing House: 2-3 (2004).
Novosibirsk, "Fundamentals of medical prevention," Educational and Methodical Manual for Students and Cadets of Advanced Training Cycles of State Professional Educational Institutions UDC 614.2-084, BBK 51.1(2)2:13-21 (2016).
Smith et al., "Organic synthesis. Science and Art," Moscow Mir 573:64 (2001).
Non-Final Office Action dated Jul. 14, 2025, in U.S. Appl. No. 18/021,907.

(Continued)

*Primary Examiner* — Andrea Olson
*Assistant Examiner* — Benjamin M Brandsen
(74) *Attorney, Agent, or Firm* — MEDLER FERRO WOODHOUSE & MILLS PLLC

(57) ABSTRACT

5'-O-Phenylacetyluridine effectively delivers both phenylacetate and uridine to a subject. It can be used to treat hepatic encephalopathy and genetic disorders of the hepatic nitrogen cycle.

10 Claims, 3 Drawing Sheets

(56) References Cited

OTHER PUBLICATIONS

International Search Report issued in PCT/US2021/050149, dated Dec. 23, 2021.
International Search Report issued in PCT/US2021/061053, dated Feb. 7, 2022.
International Search Report issued in PCT/US2022/014874, dated May 6, 2022.
Pubchem, Substance Record for SID 45985391, available date: Dec. 5, 2007. https://pubchem.ncbi.nlm.nih.gov/substance/45985391.
Pubchem, Substance Record for SID 47237025, available date: Jun. 22, 2015. https://pubchem.ncbi.nlm.nih.gov/substance/47237025.
Ashour et al., "5-(m-Benzyloxybenzyl)barbituric acid acyclonucleoside, a uridine phosphorylase inhibitor, and 2', 3',5'-tri-O-acetyluridine, a prodrug of uridine, as modulators of plasma uridine concentration. Implications for chemotherapy," Biochemical Pharmacology, 51(12):1601-1611 (1996).
Banker, G.S. et al, "Modern Pharmaceutics, 3ed.", Marcel Dekker, New York, 1996, p. 596.
Latvijas PSR Zinatnu akademijas vestis, Kimijas serija: 745-746 (1977).
Livingston et al., "Body surface area prediction in normal-weight and obese patients", American Journal of Physiology—Endocrinology and Metabolism 281:E586-E591 (2001).
Mosley et al., "Mutant Clone of Chinese Hamster Ovary Cells Lacking 3-Hydroxy-3-methylglutaryl Coenzyme A Reductase," The Journal of Biological Chemistry 258(22):13875-13881 (1983).
Wolff, Manfred E. "Burger's Medicinal Chemistry, 5ed, Part I", John Wiley & Sons, 1995, pp. 975-977.
Zheng et al., "Production of N-acetylglucosamine by Biosynthesis," Beijing University of Chemical Technology: A Master's Thesis (2019); English Abstract on pp. 7-8.
Notice of Allowance in US Appl. No. 18/021, 907, dated Nov. 13, 2025.
Non-Final Office Action in U.S. Appl. No. 18/547,053, dated Dec. 19, 2025.
Notice of Allowance in U.S. Appl. No. 18/547,053, dated Apr. 9, 2026.

* cited by examiner

5'-O-PHENYLACETYLURIDINE AND THERAPEUTIC USE

BACKGROUND OF THE INVENTION

Phenylacetate and its precursor phenylbutyrate have important therapeutic applications, exploiting the activity of phenylacetate as an ammonia scavenger for elimination of excess ammonia in conditions such as hepatic encephalopathy and genetic disorders of the nitrogen cycle. Furthermore, additional activities of phenylacetate as a molecular chaperone to mitigate protein misfolding in the endoplasmic reticulum, and as an inhibitor of histone deacetylation have been harnessed for therapeutic benefit in various other diseases and disease models.

In conditions such as hepatic encephalopathy, excess ammonia is not the sole factor in disease pathogenesis and progression, as neuroinflammation and diminished mitochondrial function are also involved. The pyrimidine nucleoside uridine has broad anti-inflammatory activity, both systemically and in the brain, and provides support for cells, including neurons, with defective mitochondrial electron transport and oxidative phosphorylation. Oral 2',3',5'-tri-O-acetyluridine increases plasma uridine more effectively than oral uridine itself, in part because of the dose-limiting side effects of oral uridine.

SUMMARY OF THE INVENTION

This invention provides the compound 5'-O-Phenylacetyluridine. It provides a method of treating or preventing a condition selected from the group consisting of hepatic encephalopathy and a genetic disorder of the hepatic nitrogen cycle in a subject comprising administering to the subject an amount of a compound of this invention effective to treat the disorder. This invention also provides a compound of this invention for use in treating or preventing, or for the manufacture of a medicament for treating or preventing a condition selected from the group consisting of hepatic encephalopathy and a genetic disorder of the hepatic nitrogen cycle. And it provides a pharmaceutical composition comprising a compound of this invention and a pharmaceutically acceptable carrier.

The compound 5'-O-Phenylacetyluridine (PAU), when administered orally has been found to increase plasma uridine more effectively than uridine itself. And to deliver phenylacetate into the bloodstream more effectively than phenylbutyrate, a precursor that is favored over phenylacetate as a drug due to the unpleasant odor of phenylacetate, and which is approved by FDA for use as an ammonia scavenger.

DETAILED DESCRIPTION OF THE INVENTION

Figure 1:
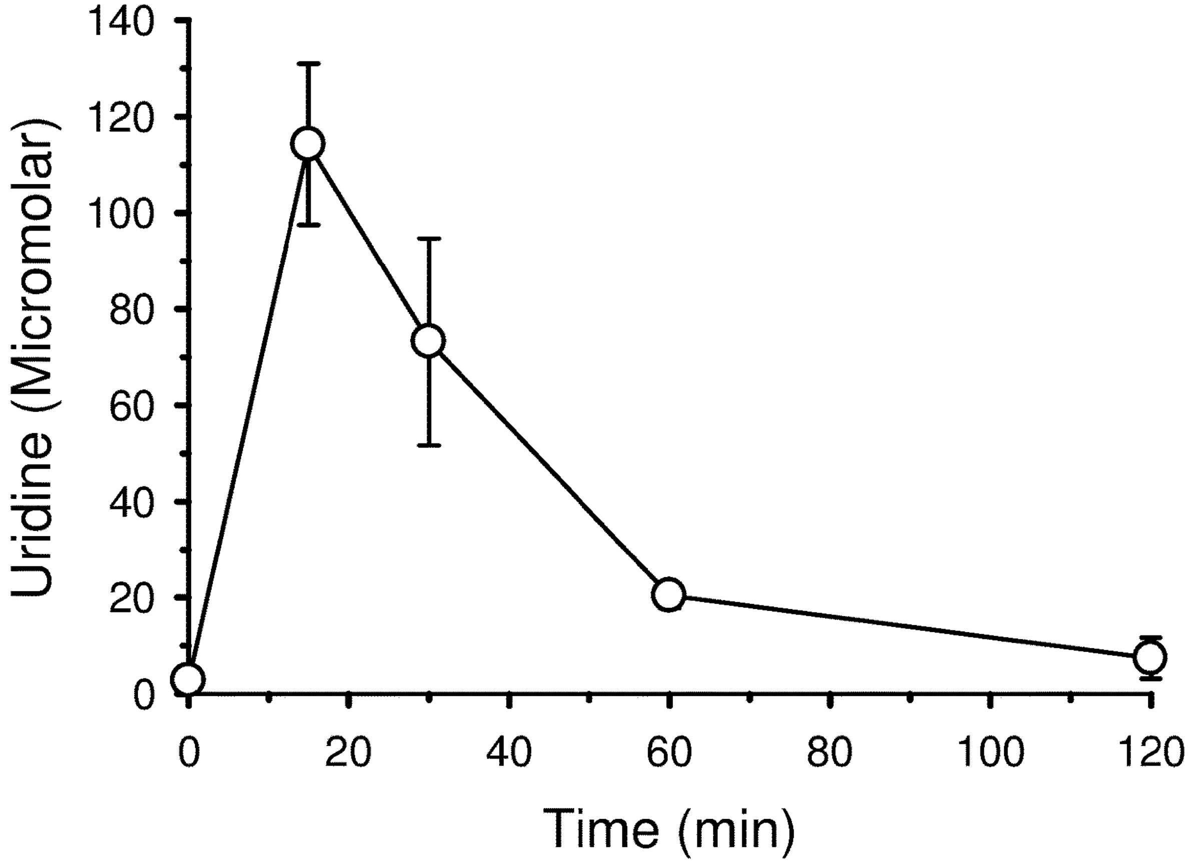
FIG. 1: Plasma uridine in mice after oral administration of 5'-phenylacetyluridine

As used herein the transitional term "comprising" is open-ended. A claim utilizing this term can contain elements in addition to those recited in such claim. Thus, for example, the claims can read on treatment regimens that also include other therapeutic agents or therapeutic virus doses not specifically recited therein, as long as the recited elements or their equivalent are present.

Abbreviations:

PAU or 5'-PAU: 5'-O-Phenylacetyluride, also known as 5'-phenylacetyluridine
PA: Phenylacetate
PB: Phenylbutyrate
NaPB: Sodium phenylbutyrate
DMF: Dimethylformamide
TLC: Thin-layer chromatography
DMSO: Dimethyl sulfoxide
HPMC: Hydroxypropylmethyl cellulose
LPS: Lipopolysaccharide
TNF: Tissue necrosis factor

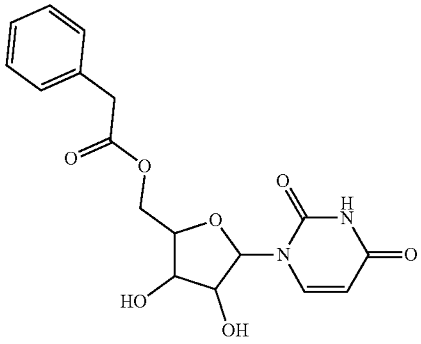

5'-PAU
Molecular Formula = $C_{17}H_{18}N_2O_7$
Formula Weight = 362.33402
LogP = 0.51 +/- 0.61

In addition to providing therapeutic benefits derived from concurrent delivery of uridine and phenylacetate, there are important safety factors achieved by using uridine in combination with phenylacetate because the uridine can attenuate the metabolic imbalances caused by phenylacetate or its precursor phenylbutryate.

In accordance with the method, the compound for use, the use, and the pharmaceutical composition of this invention any conventional disorder characterized by the potential for benefit imparted by phenylacetate and uridine in a mammalian subject can be treated or prevented. Such conditions are selected based on any of several known activities and mechanisms of action of phenylacetate or its precursor phenylbutyrate, in which broad tissue-neuroprotective and tissue protective activity imparted by therapeutic doses of uridine are also indicated. In one embodiment, Hepatic Encephalopathy is treated with 5'-phenylacetyluridine, with the phenylacetate moiety scavenging excessive circulating and tissue ammonia associated with this condition, and uridine providing direct neuroprotective activity against neuroinflammation and mitochondrial dysfunction that also characterize hepatic encephalopathy. Hepatic encephalopathy at all stages of severity, from acute crisis to minimal clinical symptoms, is treated with 5'-phenylacetyluridine. For severe hepatic encephalopathy, doses ranging 1 up to 9 grams per square meter of body surface area of phenylacetyluridine are administered once to three times per day, with the dose selected depending on severity of ammonia overload in a particular patient.

Right ventricular failure and pulmonary artery remodeling in pulmonary hypertension involves pathologic metabolic remodeling affecting the heart and pulmonary artery, with excessive aerobic glycolysis, similar to the Warburg effect in many cancers. Phenylacetate inhibits pyruvate carboxylase, partially mitigating pathological aerobic glycolysis. Furthermore, uridine improves inotropy in pressure-overloaded myocardium. Therefore, as a single agent, or in combination with uridine triacetate for modulating uridine/phenylacetate ratios, 5'-phenylacetyluridine provides more complete protection of the right ventricle in pulmonary hypertension than either agent alone; right ventricular failure is the primary cause of death in people with primary pulmonary hypertension. For treatment of pulmonary hypertension, doses of ranging from 1 to 5 grams per square meter of body surface area are administered one to three times per day.

In accordance with this invention the compound can be administered to any mammalian subject. In one embodiment the mammalian subject is a human subject. In accordance with this invention, any conventional route of administration can be utilized. Preferably the compound is administered orally. The skilled practitioner can titrate to optimize the dosage for a particular patient. Typically the compound is administered orally to a human patient in a dose of from 1 to grams per square meter of body surface area. Usually the dose is administered 1 to 3 times per day.

PB is generally administered to patients as a sodium salt (Buphenyl®) at doses of 5-25 g/day. Since sodium comprises 12% sodium weight/weight and therefore a 10 g/day NaPB treatment would result in 1.2 g of sodium intake. The recommended daily intake of sodium is 2.3 g and excessive sodium intake is associated with increased incidence of hypertension, myocardial infarction and stroke (Strazzullo, D'Elia et al. 2009; Frieden and Briss 2010). One object of this invention is to provide a biologically active derivative of PB in a form which does not add excessive sodium intake. This is accomplished by means of ester linkage with uridine.

Glutamine depletion due to PB represents an additional metabolic compromise in mammals that do not have a urea cycle disorder or excessive levels of ammonia. Glutamine depletion and resulting loss of ammonia can lead to a depletion of pyrimidines (uridine and cytidine) because pyrimidine synthesis requires glutamine. Pyrimidine synthesis can be altered by levels of glutamine or dietary protein (Monks, Chisena et al. 1985; Nelson, Qureshi et al. 1993; Zaharevitz, Grubb et al. 1993). The use of a uridine ester-linked PB-related derivative provides uridine and thus prevents uridine depletion.

The invention will be better understood by reference to the following examples, which illustrate but do not limit the invention described herein.

EXAMPLES

Example 1: Preparation of 5'-O-Phenylacetyluridine

1. Preparation of 2',3'-O-Cyclohexylideneuridine

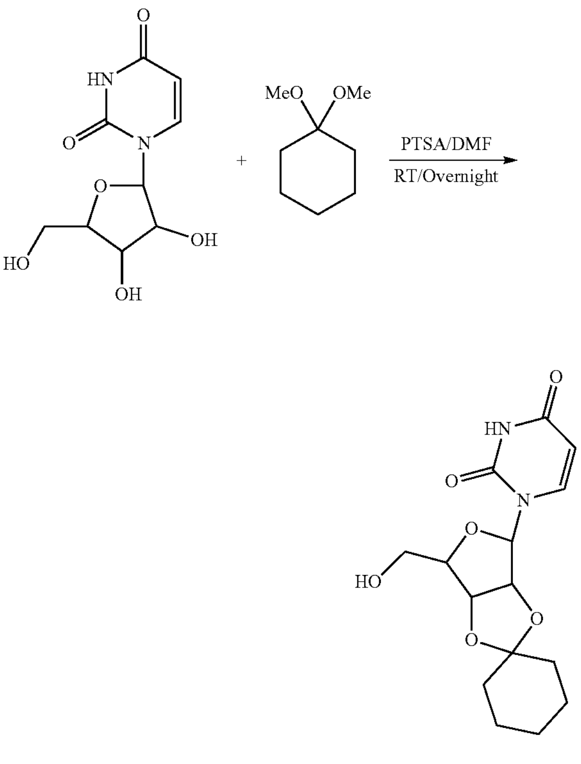

Uridine (50 g, 205 mmoles) was dissolved in anhydrous DMF (250 mL) and a catalytic amount of para-toluenesulfonic acid (1.8 grams) was added while stirring under argon at room temperature. After 20 minutes, 31 mL, or 2.0 equivalents, of 1,1-dimethoxycyclohexane was added. The reaction mixture was stirred at room temperature under argon overnight. The reaction was checked by TLC (EtOAc, $R_f$=0.2) for completion and 250 mL of methanol was added and then evaporated twice. The crude reaction mixture was purified by flash chromatography using silica gel and ethyl acetate to yield 33 grams of the desired product (50% yield). $^1$H NMR (400 MHz, DMSO-$d_6$) δ 1.34-1.69 (m, 10H), 3.55 (broad s, 2H) 4.03-4.05 (m, 1H), 4.73 (d, 1H, J=3.6 Hz), 4.86-4.88 (m, 1H), 5.06 (s, OH), 5.61 (d, 1H, J=8.1 Hz), 5.82 (dd, 1H, J=2.6, 7.0 Hz), 7.76-7.80 (m, 1H), 11.35 (s, NH)

2. Preparation of 2',3'-O-Cyclohexylidene-5'-O-phenylacetyluridine

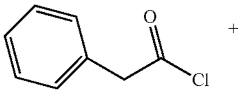

-continued

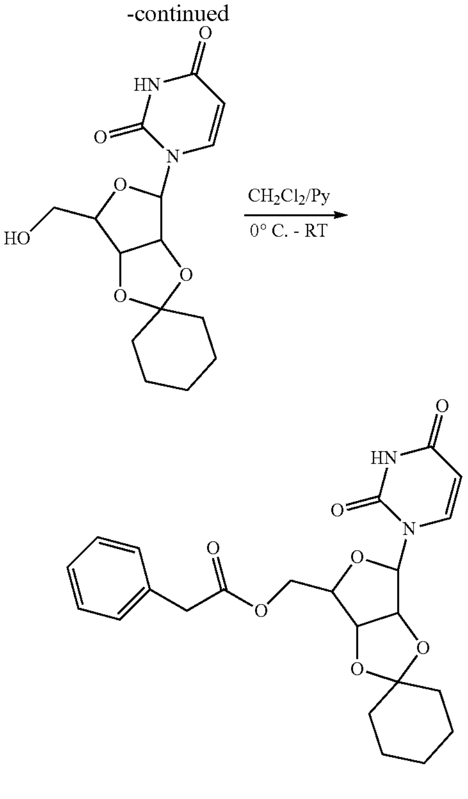

Under argon, 2',3'-O-cyclohexylideneuridine (26.0 g, 84.4 mmoles) was dissolved in 250 mL of anhydrous $CH_2Cl_2$, 125 mL of pyridine was added, and the mixture was cooled to 0° C. Then, phenylacetyl chloride (16 mL, 1.2 eq) was added dropwise over 30 minutes. The reaction mixture was stirred at 0° C. for 4 hrs. and at room temperature for another 4 hrs. Completion of the reaction was verified by TLC (EtOAc, $R_f$=0.6). The reaction was quenched with methanol and evaporated to dryness. The residue was dissolved in EtOAc (500 mL) and washed with 0.1 N HCl, 0.05 N HCl, water, saturated $NaHCO_3$, and finally with water. The crude product was purified by flash chromatography using silica gel and 50% EtOAc/hexane to give 30 g of the desired product (85% yield). $^1$H NMR (400 MHz, DMSO-$d_6$) δ 1.33-1.69 (m, 10H), 3.69 (s, 2H), 4.19-4.24 (m, 3H), 4.73-4.74 (m, 1H), 4.88 (dd, 1H, J=2.2, 6.6 Hz), 5.61 (d, 1H, J=8.1 Hz), 5.77 (d, 1H, J=1.9 Hz), 7.24-7.32 (m, 5H), 7.60 (d, 1H, J=8.1 Hz), 11.42 (s, NH).

3. Preparation of 5'-O-Phenylacetyluridine

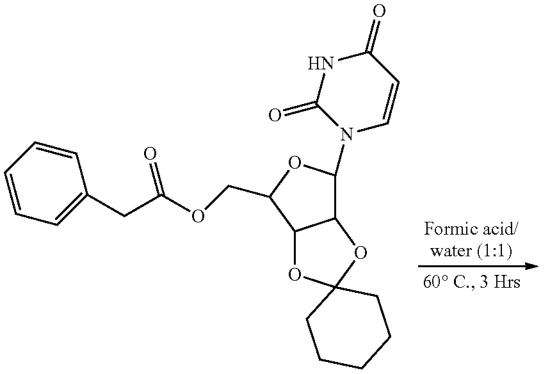

-continued

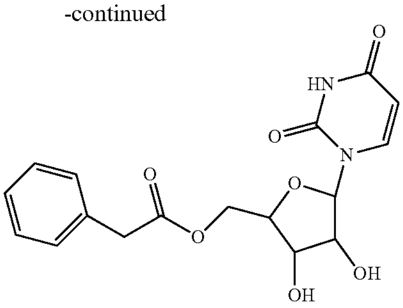

2',3'-O-Cyclohexylidene-5'-O-phenylacetyluridine (32.80 g, 77.1 mmoles) was dissolved in 300 mL of a 1:1 mixture of formic acid and water. The reaction mixture was heated at 65-70° C. for 4 hrs. differs from reaction figure TLC (ethyl acetate) confirmed the consumption of the starting material. Water and formic acid were removed by evaporation under vacuum. The crude product was dissolved in water (250 mL) and evaporated to dryness twice. Purification by flash chromatography using silica gel and ethyl acetate yielded 15.1 grams (56%) of the desired product. Attempts to recrystallize the product from solvents ethyl acetate/hexane, ethyl ether/hexane, methanol/hexane, ethanol/hexane, ethanol/ethyl ether, acetone/hexane, ethanol/ethyl ether, methanol/ethyl ether were unsuccessful. Analysis by LC-MS showed that 92% of the total absorbance of light at $\lambda_{230}$ corresponded to the product. $^1$H NMR (400 MHz, DMSO-$d_6$) δ 3.71 (ABq, 2H), 3.85-4.05 (m, 3H), 4.15-4.30 (m, 2H), 5.28 (d, OH, J=5.1 Hz), 5.43 (d, OH, J=6.5 Hz), 5.61 (d, 1H, J=8.1 Hz), 5.72 (d, 1H, J=5.1 Hz), 7.24-7.31 (m, 5H), 7.46 (d, 1H, J=8.1 Hz), 11.35 (s, NH). Melting point 55-57° C.

Example 2: Plasma Uridine and Uracil Pharmacokinetics after Oral Administration of 5'-O-phenylacetyluridine (PAU)

Chemical(s): HPMC (Hydroxypropylmethyl cellulose; SIGMA-Aldrich: cat #H3785, CAS 9004-65-3), 5'-O-Phenylacetyluridine (PAU, lot 432-132)

Vehicle: Aqueous HPMC (0.75%) was used as a suspending vehicle for oral administration.

Dosing Formulation: PAU was added to 0.75% HPMC and homogenized to eliminate clumps. The suspension were made up to the desired volume and concentration and sonicated to disaggregate any small leftover clumps into fine particles. Suspensions were stored at 4° C. until use. Suspensions were used within 24 hrs of preparation.

Dosing: Mice received a dose of 587 mg/Kg PAU (molar equivalent to 400 mg/kg uridine) gavaged at 0.02 ml/g body weight.

Animals: Female CD-1 mice.

| Species | Strains | Gender | Number | Age and Weight Range at Shipment | Vendor | Diet and Housing |
|---|---|---|---|---|---|---|
| Mouse | CD-1 | Females | 9 | ~26-30 g | Envigo | Harlan Teklad 2016, ad libitum, housed 5/cage |

The general initial layout for the experiment involved gavaging groups of 6 mice with PAU and obtaining blood samples at several times points thereafter (3 mice were bled for 2 time points (15 and 60 minutes), and another 3 mice were bled for the other 2 time points (30 and 120 minutes). Each experiment included an HPMC (vehicle only) time point with 3 mice to establish a baseline for blood uridine

| Group No. | No. of Animals | Bleeding Time After Dosing |
|---|---|---|
| PAU | 6 | 15, 30, 60, & 120 min |
| HPMC | 3 | — |

Blood samples were collected into plasma separation tubes, which were centrifuged immediately after blood collection, and aliquots of plasma were frozen for subsequent processing. Plasma was later deproteinated, and uridine and uracil were quantified by liquid chromatography using UV absorbance detection and mass spectrometry.

Delivery of uridine into the bloodstream was assessed by monitoring plasma uridine and the sum of uridine and uracil [uridine+uracil], as uracil is the first product in enzymatic degradation of uridine. Mice convert administered uridine to uracil more rapidly and extensively than do humans, so that uridine+uracil provides a better index for translation of dosing and pharmacokinetics to humans than does measurement of uridine alone.

Figure 2:
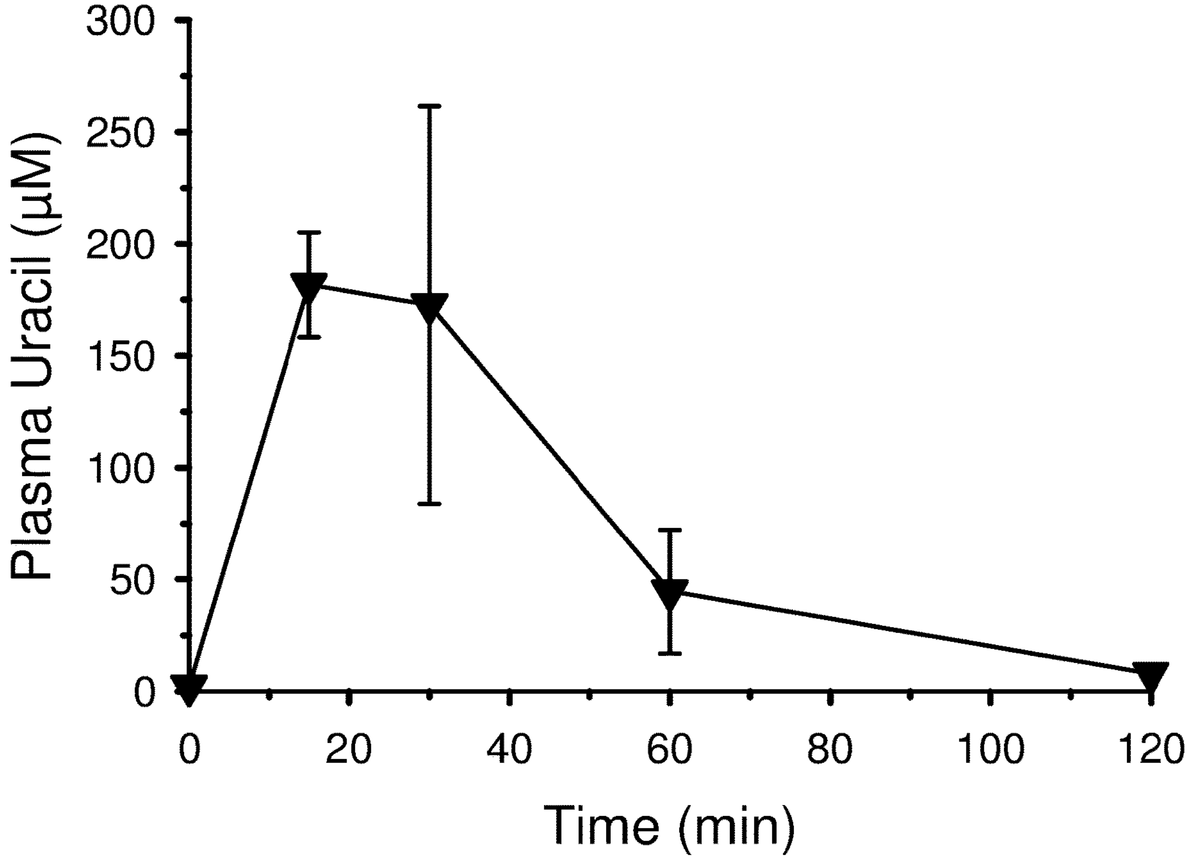
FIG. 2: Plasma uracil in mice after oral administration of 5'-phenylacetyluridine
Figure 3:
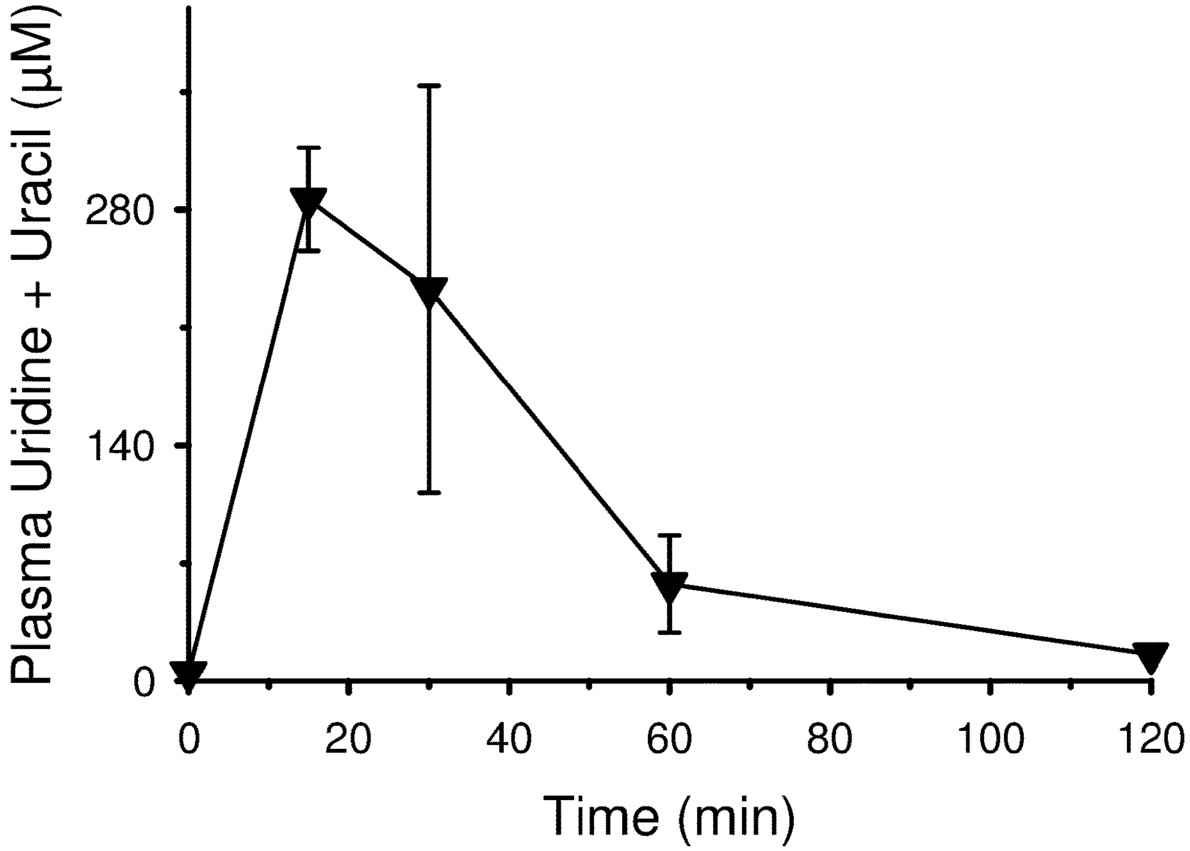
FIG. 3: Plasma uridine+uracil in mice after oral administration of 5'-phenylacetyluridine

Plasma uridine, uracil and [uridine+uracil] concentrations after administration of PAU are shown in FIGS. 1, 2 and 3 respectively.

The delivery of phenylacetate into the bloodstream after oral administration of PAU was also assessed. Sodium phenylbutyrate is used in clinical practice as an ammonia scavenger in hepatic encephalopathy or genetic nitrogen cycle disorders, or as a chaperone or histone deacetylase inhibitor. It is predominantly metabolized to phenylacetate via beta-oxidation in the liver, and phenylacetate mediates the therapeutic benefits of phenylbutyrate. PAU was administered orally at a dose equimolar to 200 mg/kg sodium phenylbutyrate. Female BALB/c mice (n=3-5 group) were given test compounds p.o. and after 30 minutes were retro-orbitally bled to obtain plasma. The table summarizing the comparative bioavailability of PAU and sodium phenyulbutyrate derivatives indicates the maximum concentration ($C_{Max}$) obtained in serum after equimolar oral administration of these compounds aw an index of bioavailability. An equimolar dose or uridine was used as a comparator for efficiency of delivery of uridine into the circulation by oral administration of PAU.

TABLE 1

Plasma concentrations of uridine, PB and respective metabolites after oral administration of sodium phenylbutyrate or PAU

| Compound | Uridine | Uracil | PB | PA |
|---|---|---|---|---|
| NaPB | NA | NA | 26 | 401 |
| PAU | 76 | 159 | <1 | 1281 |
| Uridine | 10 | 24 | NA | NA |

Plasma concentrations units are micromoles/liter (µM)
NaPB=sodium phenylbutryate
PB=phenylbutyrate
PA=phenylacetate
PAU=5'-O-Phenylacetyluridine Oral PAU was substantially more effective than an equimolar dose of oral sodium phenylbutyrate for raising plasma phenylacetate concentrations, yielding a >3-fold higher concentration of circulating phenylacetate at 30 minutes after administration. Furthermore, PAU elevated plasma uridine and uracil better than did and equimolar dose of oral uridine.

Example 3: Anti-Inflammatory Effects of 5'-O-Phenylacetyluridine (PAU)

Injection of bacterial cell wall constituent lipopolysaccharide (LPS) has been used as a model of inflammation. The inflammatory cascade can lead to cellular and organ damage when unchecked. Tissue necrosis factor α (TNFα) is strongly induced during inflammation and attenuating this response can be protective in numerous diseases including rheumatoid arthritis, psoriasis, vasculitis and Alzheimer's disease.

Female BALB/c mice 41 weeks of age (n=7-8/group) were treated with Vehicle (0.75% HPMC) or PAU p.o. and 30 minutes later LPS (2.5 mg/kg i.p.) was administered. One hour after LPS, mice were sacrificed and blood was collected for measurement of plasma TNFα.

TABLE 2

Effect of PAU on plasma TNFα changes due to LPS

| Treatment | TNF α (pg/ml) ± SEM |
|---|---|
| Vehicle | 15,981 ± 2,951 |
| PAU (165 mg/kg) | 10,068 ± 2,583 |
| PAU (331 mg/kg) | 7,034 ± 1,236 + |

+ Indicate $p < .05$ compared to Vehicle control.

PAU provides significant anti-inflammatory effect in the LPS-induced elevation of plasma TNFα.

What is claimed is:

1. A compound, 5'-O-Phenylacetyluridine.

2. A method of treating a condition in a mammalian subject, wherein the condition is selected from the group consisting of hepatic encephalopathy and a genetic disorder of the hepatic nitrogen cycle, comprising administering to the subject an effective amount of the compound of claim 1, thereby treating the condition.

3. The method of claim 2, wherein the administration is oral.

4. The method of claim 3, wherein the mammalian subject is a human subject.

5. The method of claim 4, wherein the effective amount is from 1 to 5 grams per square meter of body surface area, administered one, two or three times daily.

6. A pharmaceutical composition comprising a pharmaceutically acceptable carrier and the compound of claim 1 in an amount effective to treat a condition in a mammalian subject, wherein the condition is selected from the group consisting of hepatic encephalopathy and a genetic disorder of the hepatic nitrogen cycle.

7. The pharmaceutical composition of claim 6, wherein the pharmaceutical composition is formulated for oral administration to the mammalian subject.

8. The pharmaceutical composition of claim 6, wherein the mammalian subject is a human subject.

9. The pharmaceutical composition of claim 8, wherein the pharmaceutical composition is formulated for oral administration to the human subject.

10. The pharmaceutical composition of claim 9, formulated for administration of the compound in a dose of from 1 to 5 grams per square meter of body surface area, administered one, two or three times daily.

* * * * *